(12) United States Patent
Yang et al.

(10) Patent No.: US 11,751,962 B1
(45) Date of Patent: Sep. 12, 2023

(54) SLAVE DRIVING DEVICE OF INTERVENTIONAL SURGICAL ROBOT AND ELONGATED MEDICAL INSTRUMENT DELIVERY METHOD

(71) Applicant: SHENZHEN INSTITUTE OF ADVANCED BIOMEDICAL ROBOT CO., LTD., Guangdong (CN)

(72) Inventors: Liangzheng Yang, Guangdong (CN); Wenyong Ren, Guangdong (CN)

(73) Assignee: SHENZHEN INSTITUTE OF ADVANCED BIOMEDICAL ROBOT CO., LTD., Shenzhen (CN)

( * ) Notice: Subject to any disclaimer, the term of this patent is extended or adjusted under 35 U.S.C. 154(b) by 0 days.

(21) Appl. No.: 18/082,558

(22) Filed: Dec. 15, 2022

Related U.S. Application Data

(63) Continuation of application No. PCT/CN2022/127423, filed on Oct. 25, 2022.

(30) Foreign Application Priority Data

Aug. 8, 2022 (CN) .......................... 202210944474.6

(51) Int. Cl.
| | | |
|---|---|---|
| *A61B 34/37* | (2016.01) | |
| *A61B 34/00* | (2016.01) | |
| *A61M 25/01* | (2006.01) | |
| *A61B 34/30* | (2016.01) | |
| *A61B 17/00* | (2006.01) | |

(52) U.S. Cl.
CPC .............. *A61B 34/37* (2016.02); *A61B 34/74* (2016.02); *A61M 25/0113* (2013.01); *A61B 2017/00398* (2013.01); *A61B 2034/301* (2016.02); *A61B 2034/304* (2016.02)

(58) Field of Classification Search
CPC ... A61B 34/37; A61B 34/74; A61B 2034/301; A61B 2034/304; A61B 2017/00398; A61M 25/0113
USPC ............................................................ 606/1
See application file for complete search history.

(56) References Cited

FOREIGN PATENT DOCUMENTS

| | | |
|---|---|---|
| CN | 114224493 A | 3/2022 |
| CN | 114391948 A | 4/2022 |
| CN | 114391961 A | 4/2022 |

OTHER PUBLICATIONS

1st Office Action of counterpart Chinese Patent Application No. 202210944474.6 dated Sep. 9, 2022.

(Continued)

*Primary Examiner* — Aaron F Roane

(57) ABSTRACT

The present application relates to the technical field of medical robots, and in particular, to a slave driving device of an interventional surgical robot and an elongated medical instrument delivery method. The slave driving device includes: a frame; a first driving mechanism, fixedly arranged on the frame to clamp one end of an elongated medical instrument to deliver the elongated medical instrument; and a second driving mechanism, movably arranged on the frame to clamp the other end of the elongated medical instrument to deliver the elongated medical instrument through movement on the frame. Since only the second driving mechanism is able to move on the frame, the overall size of the slave driving device is reduced by using a reasonable structural design, and the occupied space and the overall weight of the slave driving device are reduced, thereby facilitating the spatial layout of the surgical robot.

8 Claims, 7 Drawing Sheets

(56) References Cited

OTHER PUBLICATIONS

2nd Office Action of counterpart Chinese Patent Application No. 202210944474.6 dated Sep. 28, 2022.
Notice of Allowance of counterpart Chinese Patent Application No. 202210944474.6 dated Oct. 13, 2022.

SLAVE DRIVING DEVICE OF INTERVENTIONAL SURGICAL ROBOT AND ELONGATED MEDICAL INSTRUMENT DELIVERY METHOD

CROSS REFERENCE TO RELATED APPLICATIONS

The present application is a Continuation Application of PCT Application No. PCT/CN2022/127423 filed on Oct. 25, 2022, which claims priority to Chinese Patent Application No. 202210944474.6, filed with the China National Intellectual Property Administration on Aug. 8, 2022 and entitled "SLAVE DRIVING DEVICE OF INTERVENTIONAL SURGICAL ROBOT", which is incorporated herein by reference in its entirety.

TECHNICAL FIELD

The present application relates to the technical field of medical robots, and in particular, to a slave driving device of an interventional surgical robot and an elongated medical instrument delivery method.

BACKGROUND

Interventional therapy is a minimally invasive treatment using modern high-tech means, which under the guidance of medical imaging device, introduces precision instruments such as specially-made catheters or guide wires into the human body, to perform diagnosis and local treatment on pathologies in the body.

Existing interventional surgical robots deliver catheters through coordinated movement of a plurality of driving devices. The inventors realized that in the process of catheter delivery, in order to ensure sufficient motion travel of the plurality of driving devices in a delivery direction of the catheter, the device should have sufficient internal space, resulting in an extremely large overall volume and bulkiness of the device, which is not conducive to spatial layout of the surgical robot.

To-be-resolved Problem

An object of the present application mainly is to provide a slave driving device of an interventional surgical robot and an elongated medical instrument delivery method, aiming to solve the foregoing technical problems that the existing device has an extremely large overall volume and is bulky, which is not conducive to spatial layout of the surgical robot.

Technical Solutions

The present application provides the following technical solution: a slave driving device of an interventional surgical robot, including:

a frame;

a first driving mechanism, fixedly arranged on the frame to clamp one end of an elongated medical instrument to deliver the elongated medical instrument;

a second driving mechanism, movably arranged on the frame to clamp the other end of the elongated medical instrument to deliver the elongated medical instrument through movement on the frame;

a driving assembly, installed on the frame and used for driving the second driving mechanism to move in a delivery direction of the elongated medical instrument; and a detection component, arranged on the driving assembly to detect whether the elongated medical instrument between the first driving mechanism and the second driving mechanism is straightened; where at the beginning of operation, the elongated medical instrument between the first driving mechanism and the second driving mechanism is in a bent state, and is delivered by the first driving mechanism until the detection component detects that the elongated medical instrument between the first driving mechanism and the second driving mechanism is straightened, and the second driving mechanism is activated to deliver the rear end of the elongated medical instrument, the second driving mechanism delivering the elongated medical instrument at the same speed as the first driving mechanism delivers the elongated medical instrument.

Further, the driving assembly includes a driving motor installed on the frame and a lead screw structure arranged on the frame and in transmission connection with the driving motor, and the lead screw structure is connected to the second driving mechanism to drive movement of the second driving mechanism on the frame.

Further, the lead screw structure includes a lead screw and a nut seat, the lead screw and the nut seat form a threaded fit, the driving motor is installed on the frame by using a first support plate, one end of the lead screw is arranged at the output end of the driving motor, and the other end is rotatably connected to a second support plate installed on the frame.

Further, the detection component is a pressure sensor, the nut seat is fixedly connected to a connection block, the nut seat includes a base and a sleeve shaft that sequentially passes through the pressure sensor and the connection block, and the pressure sensor is located between the base and the connection block.

Further, the driving assembly includes a driving motor installed on the frame and a synchronous belt structure arranged on the frame and in transmission connection with the driving motor, and the synchronous belt structure is connected to the second driving mechanism to drive movement of the second driving mechanism on the frame.

Further, the synchronous belt structure includes a master synchronous wheel arranged at the output end of the driving motor, a second support plate installed on the frame, a slave synchronous wheel installed on the second support plate, and a synchronous belt wound around the master synchronous wheel and the slave synchronous wheel.

Further, the first driving mechanism is installed at the end of the frame, and the driving motor is arranged at the position close to the first driving mechanism.

Further, the driving assembly is a linear module installed on the frame to drive the second driving mechanism to move in a delivery direction of the elongated medical instrument.

Further, a guide rail and a slider are installed on the frame, an extension direction of the guide rail is the same as the delivery direction of the elongated medical instrument, the slider is installed on the slider and can slide along the guide rail, and the second driving mechanism is connected to the slider by using a connection plate.

Further, sliding chutes are respectively arranged on two sides of the guide rail, the sliding chutes extend in the extension direction of the guide rail, a clamping groove is formed in the bottom of the slider, clamping protrusions are respectively arranged on two opposite side walls in the clamping groove, and when the slider and the guide rail are cooperatively installed, the surface, close to the slider, of the guide rail is clamped into the clamping groove, and the clamping protrusions are correspondingly clamped into the sliding chutes, so that the slider can slide along the guide rail.

Further, the connection plate includes a connection section, a first installation section, and a second installation section, the first installation section and the second installation section are respectively perpendicularly connected to two sides of the connection section and extend in opposite directions, the slider is installed on the first installation section, and the second driving mechanism is installed on the second installation section.

Further, a drag chain is further installed on the frame to receive a lead wire group electrically connected to the second driving mechanism, and the extension direction of the drag chain is the same as the delivery direction of the elongated medical instrument.

Further, the slave driving device further includes a movement detection component to detect a movement distance of the second driving mechanism, where the movement detection component includes a main scale installed on the frame and a read head installed on the connection plate, the main scale is arranged between the drag chain and the guide rail, the extension direction of the main scale is the same as the delivery direction of the elongated medical instrument, and the position of the read head corresponds to that of the main scale.

Further, the main scale is a grating scale or a magnetic grating scale, and the read head corresponds to the grating scale or the magnetic grating scale.

Further, the first driving mechanism is provided with an axial delivery assembly to deliver the elongated medical instrument, the axial delivery assembly includes a plurality of rollers rotatably installed on the first driving mechanism and a driving unit installed on the first driving mechanism for driving the rollers to rotate, and the plurality of rollers are arranged on two sides of the elongated medical instrument.

Further, the slave driving device includes an outer cover that covers the first driving mechanism and the second driving mechanism, where the outer cover and the first driving mechanism enclose an insulation space for receiving the axial delivery assembly.

Further, a delivery travel of the second driving mechanism is 0.3 m-1.5 m.

The present application further provides an elongated medical instrument delivery method, applied to a slave driving device of an interventional surgical robot according to any of the foregoing implementations, including:

clamping, by the first driving mechanism, one end of the elongated medical instrument, and clamping, by the second driving mechanism, the other end of the elongated medical instrument, where a catheter between the first driving mechanism and the second mechanism is in a bent state; and until the detection component detects that the elongated medical instrument between the first driving mechanism and the second driving mechanism is straightened, activating the second driving mechanism to deliver the rear end of the elongated medical instrument, the second driving mechanism delivering the elongated medical instrument at the same speed as the first driving mechanism delivers the elongated medical instrument.

Beneficial Effects

The present application provides a slave driving device of an interventional surgical robot and an elongated medical instrument delivery method, including a frame; a first driving mechanism, fixedly arranged on the frame to clamp one end of an elongated medical instrument to deliver the elongated medical instrument; and a second driving mechanism, movably arranged on the frame to clamp the other end of the elongated medical instrument to deliver the elongated medical instrument through movement on the frame. Since the first driving mechanism is fixedly arranged and only the second driving mechanism can move on the frame, the overall size of the slave driving device is reduced by using a reasonable structural design, and the occupied space and the overall weight of the slave driving device are reduced, thereby facilitating the spatial layout of the surgical robot.

Figure 1:
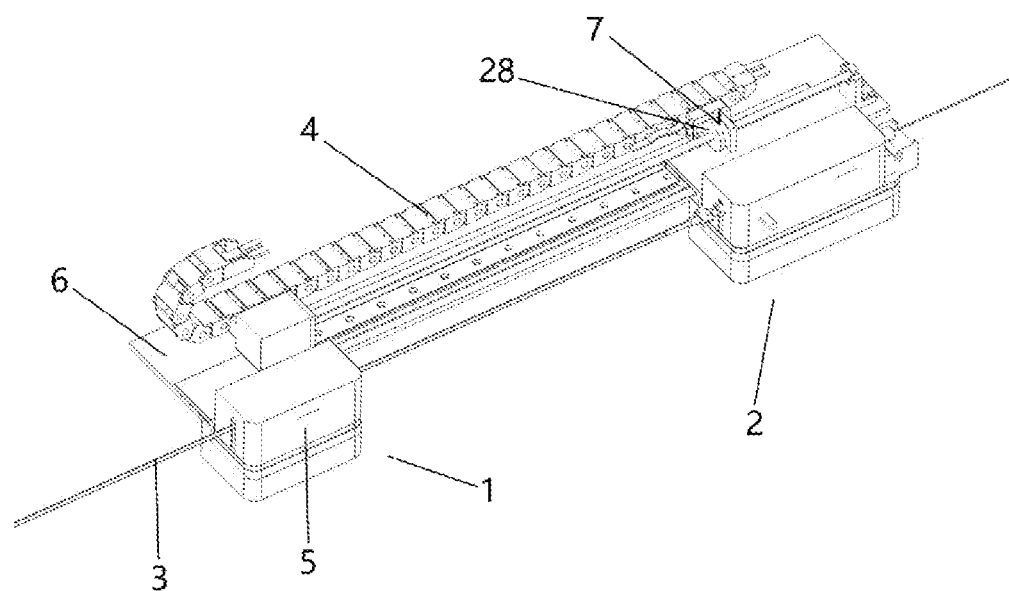
FIG. 1 is a schematic diagram of an overall structure according to the present application.

Reference numerals in the figures are as follows: 1. First driving mechanism; 11. Axial delivery assembly; 111. Roller; 112. Driving unit; 2. Second driving mechanism; 20. Driving motor; 21. First support plate; 22. Second support plate; 23. Lead screw; 24. Master synchronous wheel; 25. Slave synchronous wheel; 26. Synchronous belt; 27. Connection block; 28. Nut seat; 281. Base; 282. Sleeve shaft; 3. Catheter; 4. Drag chain; 5. Outer cover; 6. Frame; 61. Guide rail; 611. Sliding chute; 62. Connection plate; 620. Connection section; 621. First installation section; 622. Second installation section; 63. Slider; 631. Clamping protrusion; 632. Clamping groove; 7. Pressure sensor; 8. Movement detection component; 81. Main scale; 82. Read head.

DESCRIPTION OF EMBODIMENTS

It should be understood that the specific embodiments described herein are merely illustrative of the present application and are not used to limit the present application.

In the description of the present application, it should be understood that the terms "central", "longitudinal", "lateral", "length", "width", "thickness", "upper", "lower", "front", "rear", "left", "right", "vertical", "horizontal", "top", "bottom", "inner", "outer", "clockwise", "counterclockwise", and the like indicate an orientation or positional relationship based on that shown in the drawings, which is merely for ease of description and simplicity of description, and is not intended to indicate or imply that the device or element referred to must have a particular orientation, be constructed and operated in a particular orientation, and therefore cannot be construed as a limitation on the present application. In addition, the terms "first" and "second" are used only for descriptive purposes and are not to be understood as indicating or implying relative importance or implicitly indicating the quantity of technical features indicated. Therefore, the features defined with "first" and "second" may explicitly or implicitly include one or more of the features. In the description of the present application, "a plurality of" means two or more, unless otherwise specifically defined.

In the description of the present application, it should be noted that, unless otherwise explicitly specified or defined, the terms "install" and "connect" should be understood in a broad sense, for example, may be a fixed connection, may be a detachable connection, or may be an integrated connection; or may be a mechanical connection, may be a direct connection, may be a connection based on an intermediate medium, or may be an internal connection between two elements or interaction between two elements. For persons of ordinary skill in the art, the specific meanings of the foregoing terms in the present application can be understood according to specific situations.

In the present application, unless otherwise expressly specified or defined, the first feature being "above" or "below" the second feature may include the first and second features contacting directly, may also include the first and second features not contacting directly but contacting by using another feature therebetween. Further, the first feature being "on" or "above" the second feature includes the first feature being directly or obliquely on/above the second feature, or merely indicates that the horizontal height of the first feature is greater than that of the second feature. The first feature being "under" or "below" the second feature includes the first feature being directly or obliquely under/below the second feature, or merely indicates that the horizontal height of the first feature is less than that of the second feature.

Figure 2:
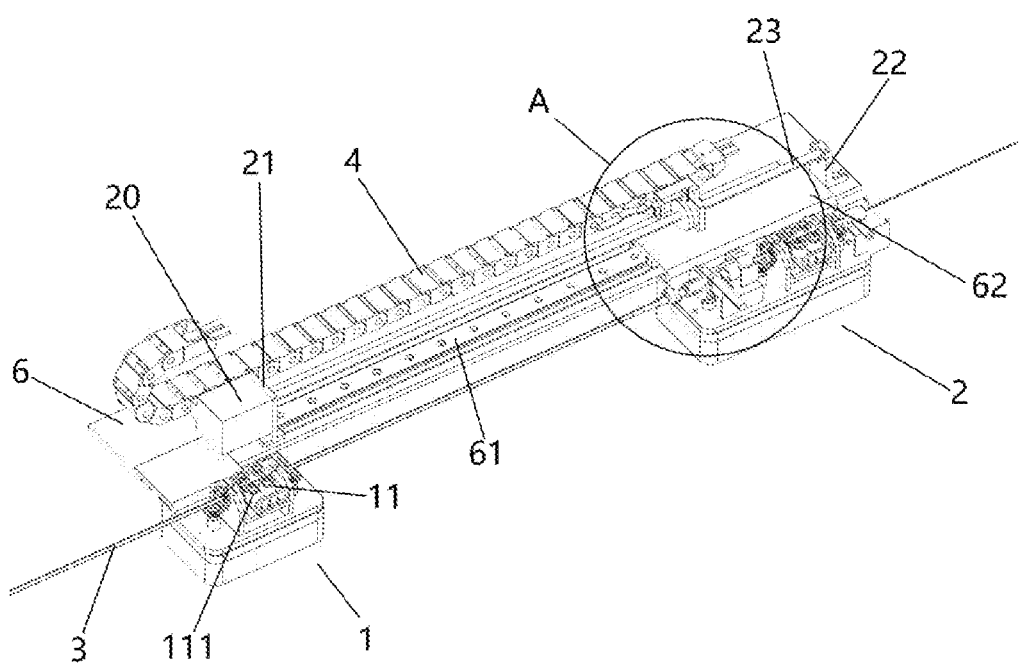
FIG. 2 is a schematic diagram of an overall structure (excluding an outer cover) according to the present application.

Referring to FIG. 1 and FIG. 2, a slave driving device of an interventional surgical robot is used for performing clamping, delivering and/or rotating operations on different elongated medical instruments (catheter 3 or guide wire), to push the elongated medical instrument (catheter 3 or guide wire) into or out of the body of a surgical patient. Specifically, the foregoing slave driving device includes a frame 6; a first driving mechanism 1, fixedly arranged on the frame 6 to clamp one end of an elongated medical instrument to deliver the elongated medical instrument; and a second driving mechanism 2, movably arranged on the frame 6 to clamp the other end of the elongated medical instrument to deliver the elongated medical instrument through movement on the frame 6. In an embodiment, the elongated medical instrument is a catheter 3, and the first driving mechanism 1 is fixed on the frame 6 to deliver the catheter 3 by using an internal structure thereof. The second driving mechanism 2 and the first driving mechanism 1 have different delivery modes to deliver the catheter 3, and the second driving mechanism 2 delivers the rear end of the catheter 3 through movement on the frame 6. In this embodiment, a delivery travel of the second driving mechanism is 0.3 m-1.5 m, and within the above range, the control accuracy of the catheter can be effectively ensured, the surgical safety can be improved, and the practicality is high.

The existing interventional surgical robot needs to keep the catheter 3 straightened all the time when delivering the catheter 3. In the existing technologies, the way to keep the catheter 3 straightened is to clamp the catheter 3 by using a plurality of driving devices, and deliver the catheter 3 through coordinated movement of the plurality of driving devices, so that the catheter 3 is always straightened. Referring to FIG. 1 and FIG. 2, in a feasible implementation, the driving assembly is provided with a detection component to detect whether the elongated medical instrument between the first driving mechanism 1 and the second driving mechanism 2 is straightened. In this embodiment, the detection component is a pressure sensor 7. When the detection component detects that the elongated medical instrument between the first driving mechanism 1 and the second driving mechanism 2 is straightened, the second driving mechanism 2 begins to move on the frame 6, and the second driving mechanism 2 delivers the elongated medical instrument at the same speed as the first driving mechanism 1 delivers the elongated medical instrument. At the beginning of operation, the front end of the catheter 3 is installed on the first driving mechanism 1, and the rear end of the catheter 3 is installed on the second driving mechanism 2. At this time, the catheter 3 remains in a bent state all the time. The first driving mechanism 1 is activated to deliver the catheter 3. Here, the first driving mechanism 1 delivers the catheter 3 by clamping a pipe body of the catheter 3, until the detection component detects that the catheter 3 between the first driving mechanism 1 and the second driving mechanism 2 is straightened, and the second driving mechanism 2 is activated to deliver the rear end of the catheter 3. It should be noted that the first driving mechanism 1 needs to deliver the pipe body of the catheter 3 at the same speed as the second driving mechanism 2 delivers the rear end of the catheter 3, so that the catheter 3 between the first driving mechanism 1 and the second driving mechanism 2 remains straightened all the time.

Figure 3:
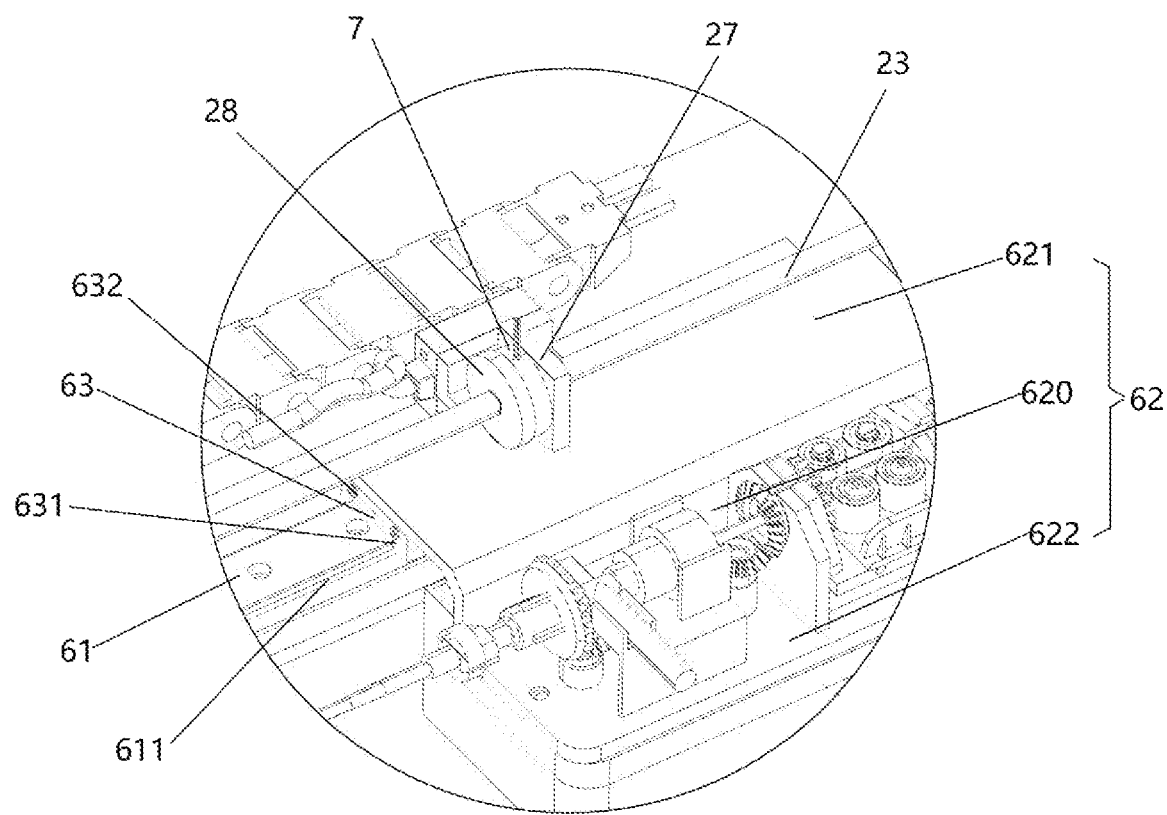
FIG. 3 is an enlarged view of A in FIG. 2.

In a feasible implementation, referring to FIG. 2 and FIG. 3, a guide rail 61 and a slider 63 are installed on the frame 6. An extension direction of the guide rail 61 is the same as a delivery direction of the elongated medical instrument. The slider 63 is installed on the guide rail 61 and can slide along the guide rail 61. The second driving mechanism 2 is connected to the slider 63 by using a connection plate 62. Specifically, sliding chutes 611 are respectively arranged on two sides of the guide rail 61, and extend in the extension direction of the guide rail 61. A clamping groove 632 is formed in the bottom of the slider 63, and clamping protrusions 631 are respectively arranged on two opposite side walls in the clamping groove 632. When the slider 63 and the guide rail 61 are cooperatively installed, the surface, close to the slider 63, of the guide rail 61 is clamped into the clamping groove 632, and the clamping protrusions 631 are correspondingly clamped into the sliding chutes 611, so that the slider 63 can slide along the guide rail 61. The connection plate 62 includes a connection section 620, a first installation section 621, and a second installation section 622. The first installation section 621 and the second installation section 622 are respectively perpendicularly connected to two sides of the connection section 620 and extend in opposite directions. The slider 63 and the second driving mechanism 2 are respectively installed on the first installation section 621 and the second installation section 622.

In a feasible implementation, a driving assembly is installed on the frame 6 to drive the second driving mechanism 2 to move in a delivery direction of the elongated medical instrument. Specifically, referring to FIG. 2 to FIG. 5, the driving assembly includes a driving motor 20 installed on the frame 6 and a lead screw structure arranged on the frame 6 and in transmission connection with the driving motor 20. The lead screw structure is connected to the second driving mechanism 2 to drive movement of the second driving mechanism 2 on the frame 6. Preferably, the lead screw structure includes a lead screw 23 and a nut seat 28. The lead screw 23 and the nut seat 28 form a threaded fit. The driving motor 20 is installed on the frame 6 by using a first support plate 21. One end of the lead screw 23 is arranged at the output end of the driving motor 20, and the other end is rotatably connected to a second support plate 22 installed on the frame 6. In this embodiment, the nut seat 28 is fixedly connected to a connection block 27; the connection block 27 is installed on the first installation section 621;

and the second driving mechanism 2 is installed on the second installation section 622. When operating, the driving motor 20 is activated. Since an internal thread of the nut seat 28 is engaged with an external thread on the lead screw 23, under the action of the external thread, the nut seat 28 drives the connection block 27 to move along the lead screw 23, so as to drive the second driving mechanism 2 to slide linearly in the delivery direction. In this embodiment, the nut seat 28 is fixedly connected to the pressure sensor 7, and the pressure sensor 7 is fixedly connected to the connection block 27. Specifically, the nut seat 28 includes a base 281 and a sleeve shaft 282. The sleeve shaft 282 sequentially passes through the pressure sensor 7 and connection block 27, and the pressure sensor 7 is located between the base 281 and the connection block 27. Specifically, when the elongated medical instrument between the first driving mechanism 1 and the second driving mechanism 2 is straightened, a delivery force of the first driving mechanism 1 to the catheter 3 is transmitted to the second driving mechanism 2 through the rear end of the catheter 3, to pull the second driving mechanism 2 to move, and meanwhile, to drive the connection block 27 to move. The connection block 27 generates pressure to the surface of the pressure sensor 7 during movement. Upon detecting a pressure signal, the pressure sensor 7 triggers the second driving mechanism 2 to move.

Figure 6:
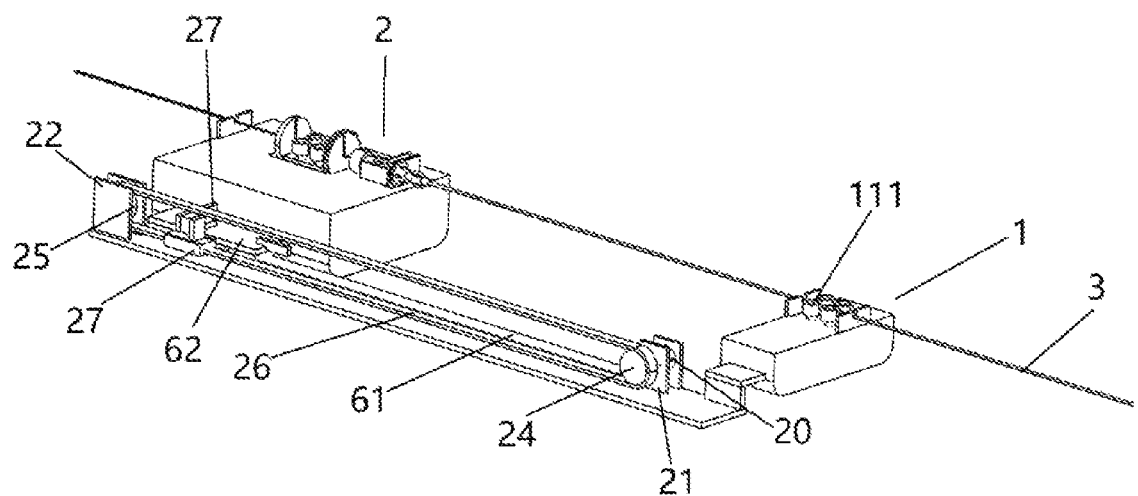
FIG. 6 is a schematic structural diagram of a driving assembly according to an embodiment.

In another feasible implementation, referring to FIG. 6, the driving assembly includes a driving motor 20 installed on the frame 6 and a synchronous belt structure arranged on the frame 6 and in transmission connection with the driving motor 20. The synchronous belt structure is connected to the second driving mechanism 2 to drive movement of the second driving mechanism 2 on the frame 6. Specifically, the driving motor 20 is installed on the frame 6 by using a first support plate 21. The synchronous belt structure includes a master synchronous wheel 24 arranged at the output end of the driving motor 20, a second support plate 22 installed on the frame 6, a slave synchronous wheel 25 installed on the second support plate 22, and a synchronous belt 26 wound around the master synchronous wheel 24 and the slave synchronous wheel 25. The synchronous belt 26 is connected to a connection plate 62 by using a connection block 27, to drive movement of the second driving mechanism 2. The master synchronous wheel 24 and the slave synchronous wheel 25 drive the synchronous belt 26 to accurately control linear movement of the second driving mechanism 2. Since the conventional rigid structure is replaced with the synchronous belt 26, the structure is simple, the mechanism is relatively light, the inertia is small, and the device can run smoothly without producing any rigid collision or impact. Meanwhile, movement of the second driving mechanism 2 on the frame 6 is linearly controlled by using a motor alone, which is suitable for clinical use.

In a feasible implementation, referring to FIG. 2, the first driving mechanism 1 is installed at the end of the frame 6, and the driving motor 20 is arranged at the position close to the first driving mechanism 1. Since the first driving mechanism 1 is arranged at the end of one side, the extension length required by the frame 6 can be shortened, making the frame 6 more portable. In addition, the motor is arranged close to the first driving mechanism 1, so that the space can be reasonably used, the overall volume of the frame 6 can be reduced, and the space utilization of the frame 6 can be improved.

In a feasible implementation, the driving assembly may be a linear module installed on the frame 6 to drive the second driving mechanism 2 to move in a delivery direction of the catheter 3. The linear module is a transmission device that converts electrical energy directly into linear motion mechanical energy without any intermediate conversion mechanism, and has the advantages such as simple structure, convenient realization of long travel, high acceleration, fast response, and high precision. The linear module can be connected to the second driving mechanism 2 to drive the second driving mechanism 2 to move linearly.

Figure 7:
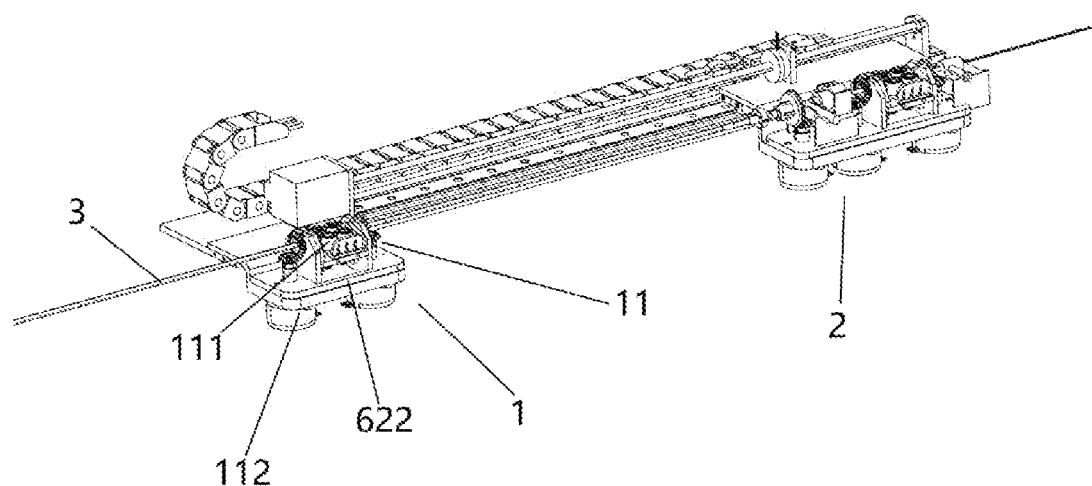
FIG. 7 is a schematic diagram of a structure of an axial delivery assembly.

In a feasible implementation, the first driving mechanism 1 is provided with an axial delivery assembly 11 to deliver the elongated medical instrument. Specifically, referring to FIG. 7, the axial delivery assembly 11 includes a plurality of rollers 111 rotatably installed on the first driving mechanism 1 and a driving unit 112 installed on the first driving mechanism 1 for driving the rollers 111 to rotate. The plurality of rollers 111 are arranged on two sides of the elongated medical instrument. Under the effect of friction between the rollers 111 and the catheter 3, the driving unit 112 drives the rollers 111 to rotate, to deliver the catheter 3. The driving unit 112 drives a rotation shaft in power connection therewith and the roller 111 installed on the rotation shaft to rotate together. During the rotation process, the roller 111 cooperates with the roller 111 on the other side to rotate together, to deliver the catheter 3. The driving unit 112 in this embodiment is arranged below the second installation section 622.

In a feasible implementation, referring to FIG. 1, the slave driving device of the interventional surgical robot further includes an outer cover 5 that covers the first driving mechanism 1 and the second driving mechanism 2. The outer cover 5 and the first driving mechanism 1 enclose an insulation space for receiving the axial delivery assembly 11.

In a feasible implementation, referring to FIG. 2, a drag chain 4 is further installed on the frame 6, the drag chain 4 is used for receiving a lead wire group electrically connected to the second driving mechanism 2. An extension direction of the drag chain 4 is the same as a delivery direction of the elongated medical instrument. In the existing technologies, the lead wire groups connected to the plurality of driving devices are all arranged in the drag chain 4, which are extremely prone to wire wear and safety hazards during movement due to dense wiring. In addition, special flexible wires need to be used, which increases costs. In the present application, since the first driving mechanism 1 is fixedly arranged on the frame 6, the lead wire group connected to the first driving mechanism 1 does not need to be placed in the drag chain 4. Preferably, in the present application, the driving motor 20 can be arranged close to the first driving mechanism 1, and the lead wire group connected to the driving motor 20 does not need to be placed in the drag chain 4, either. Therefore, only the lead wire group electrically connected to the second driving mechanism 2 needs to be placed in the drag chain 4, which can reduce the number of lead wires in the drag chain 4, reduce lead wire wear, reduce safety hazards, and reduce the use of flexible lead wires and reduces costs.

Figure 4:
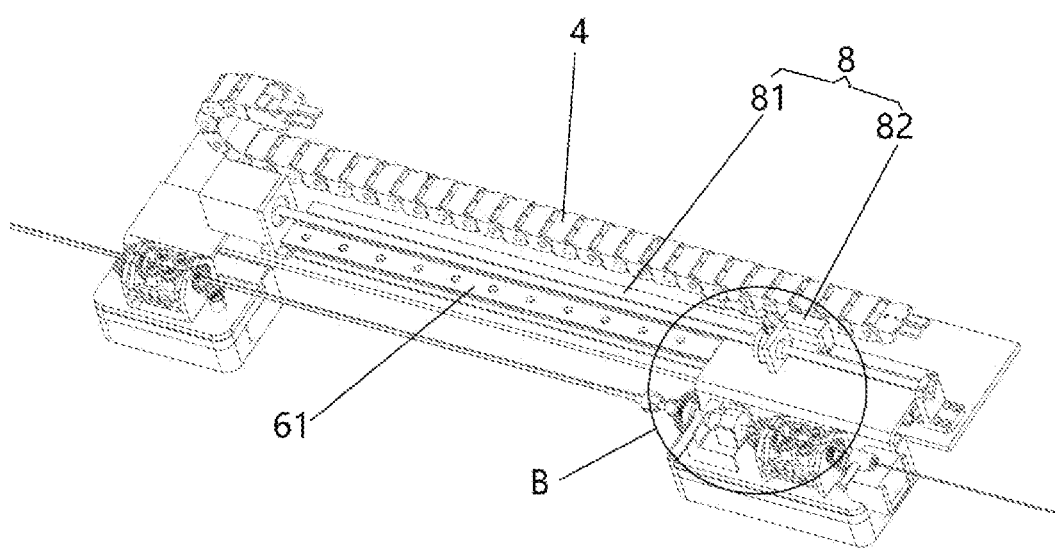
FIG. 4 is a schematic diagram of an overall structure from another angle according to the present application.
Figure 5:
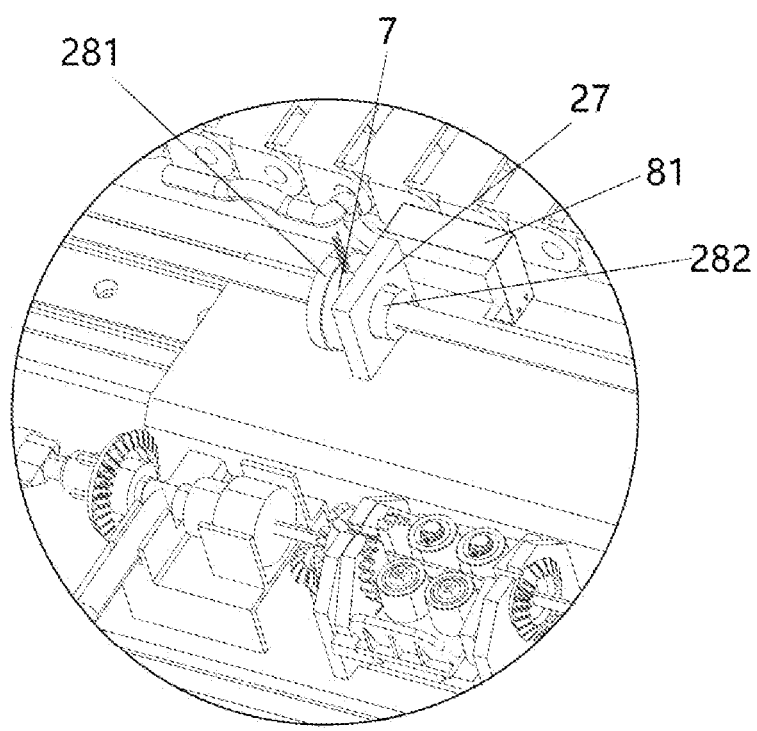
FIG. 5 is an enlarged view of B in FIG. 4.

In a feasible implementation, referring to FIG. 4 and FIG. 5, the slave driving device further includes a movement detection component 8 to detect a movement distance of the second driving mechanism. The movement detection component 8 includes a main scale 81 installed on the frame and a read head 82 installed on the connection plate. The main scale 81 is arranged between the drag chain 4 and the guide rail 61, and an extension direction of the main scale is the same as a delivery direction of the elongated medical instrument. The position of the read head 82 corresponds to that of the main scale 81. The main scale 81 may be a grating scale or a magnetic grating scale, and the read head 82 corresponds to the grating scale or the magnetic grating scale. Through the cooperation of the main scale 81 and the read head 82, the position of the second driving mechanism 2 is detected, thereby preventing a movement trail of the second driving mechanism 2 from exceeding a set value, or preventing the second driving mechanism from colliding with other components on the frame 6 to damage the second driving mechanism 2.

The foregoing descriptions are merely the preferred embodiments of the present application and are therefore not intended to limit the patent scope of the present application. Any equivalent structure or equivalent process transformation made based on the description of the specification and accompanying drawings of the present application, or directly or indirectly applied in other relevant technical fields, shall also fall within the patent scope of the present application.

What is claimed is:

1. A slave driving device of an interventional surgical robot, comprising:
    a frame;
    a first driving mechanism, fixedly arranged on the frame to clamp one end of an elongated medical instrument to deliver the elongated medical instrument;
    a second driving mechanism, movably arranged on the frame to clamp the other end of the elongated medical instrument to deliver the elongated medical instrument through movement on the frame;
    a driving assembly, installed on the frame and used for driving the second driving mechanism to move in a delivery direction of the elongated medical instrument; and
    a detection component, arranged on the driving assembly to detect whether the elongated medical instrument between the first driving mechanism and the second driving mechanism is straightened; wherein
    at the beginning of operation, the elongated medical instrument between the first driving mechanism and the second driving mechanism is in a bent state, and is delivered by the first driving mechanism until the detection component detects that the elongated medical instrument between the first driving mechanism and the second driving mechanism is straightened, and the second driving mechanism is activated to deliver the rear end of the elongated medical instrument, the second driving mechanism delivering the elongated medical instrument at the same speed as the first driving mechanism delivers the elongated medical instrument.

2. The slave driving device of an interventional surgical robot according to claim 1, wherein the driving assembly comprises a driving motor installed on the frame and a lead screw structure arranged on the frame and in transmission connection with the driving motor, and the lead screw structure is connected to the second driving mechanism to drive movement of the second driving mechanism on the frame.

3. The slave driving device of an interventional surgical robot according to claim 2, wherein the first driving mechanism is installed at the end of the frame, and the driving motor is arranged at the position close to the first driving mechanism.

4. The slave driving device of an interventional surgical robot according to claim 1, wherein the driving assembly comprises a driving motor installed on the frame and a synchronous belt structure arranged on the frame and in transmission connection with the driving motor, and the synchronous belt structure is connected to the second driving mechanism to drive movement of the second driving mechanism on the frame.

5. The slave driving device of an interventional surgical robot according to claim 1, wherein a guide rail and a slider are installed on the frame, an extension direction of the guide rail is the same as a delivery direction of the elongated medical instrument, the slider is installed on the slider to slide along the guide rail, and the second driving mechanism is connected to the slider by a connection plate.

6. The slave driving device of an interventional surgical robot according to claim 5, wherein a drag chain is further installed on the frame to receive a lead wire group electrically connected to the second driving mechanism, and the extension direction of the drag chain is the same as the delivery direction of the elongated medical instrument.

7. The slave driving device of an interventional surgical robot according to claim 6, further comprising a movement detection component to detect a movement distance of the second driving mechanism, wherein the movement detection component comprises a main scale installed on the frame and a read head installed on the connection plate, the main scale is arranged between the drag chain and the guide rail, the extension direction of the main scale is the same as the delivery direction of the elongated medical instrument, and the position of the read head corresponds to that of the main scale.

8. The slave driving device of an interventional surgical robot according to claim 1, wherein the first driving mechanism is provided with an axial delivery assembly to deliver the elongated medical instrument, the axial delivery assembly comprises a plurality of rollers rotatably installed on the first driving mechanism and a driving unit installed on the first driving mechanism for driving the rollers to rotate, and the plurality of rollers are arranged on two sides of the elongated medical instrument.

* * * * *